United States Patent [19]

Ronge et al.

[11] Patent Number: 5,705,816
[45] Date of Patent: Jan. 6, 1998

[54] PROCESS AND DEVICE FOR ANALYZING TRACES OF IMPURITIES IN A GAS SAMPLE BY MEANS OF A DIODE LASER

[75] Inventors: Catherine Ronge, Paris; Fabrice Bounaix, Luneville; Patrick Mauvais, Villepreux; Frédéric Stoeckel, Saint Martin d'Heres, all of France

[73] Assignee: L'Air Liquide, Societe Anonyme pour l'Etude et l'Exploitation des Procedes Georges Claude, Paris, France

[21] Appl. No.: 634,725

[22] Filed: Apr. 19, 1996

[30] Foreign Application Priority Data

Apr. 21, 1995 [FR] France ............... 95 04829

[51] Int. Cl.$^6$ ............................................. G01N 21/25
[52] U.S. Cl. ........................ 250/345; 250/343; 356/437
[58] Field of Search ....................... 250/338.5, 343, 250/345, 339.1, 339.13; 356/435, 436, 437

[56] References Cited

U.S. PATENT DOCUMENTS 3,805,074  4/1974  McCormack ............ 250/339.09 X
4,410,273  10/1983 Mantz et al. ............ 250/339.07 X
5,026,991  6/1991  Goldstein et al. .
5,445,964  8/1995  Lee et al. ............ 250/343 X

FOREIGN PATENT DOCUMENTS

26 35 171  2/1978  Germany.
1-23142    1/1989  Japan ................... 250/345

*Primary Examiner*—Edward J. Glick
*Attorney, Agent, or Firm*—Burns, Doane, Swecker & Mathis, LLP

[57] ABSTRACT

The invention relates to a process for analyzing traces of at least one impurity in a gas sample, by absorption by the impurity to be detected of a light beam emitted by a semiconductor diode laser, the beam emitted by the diode being split into at least two branched beams, one called the measurement beam which passes through the gas sample to be analyzed in a multipassage cell before being focused onto a measurement photodetector, another branched beam, called the reference beam, being along a reference path and directly focused onto a reference photodetector without encountering the gas sample, in which process the gas sample is at a pressure at least equal to atmospheric pressure, and a modulation of the supply current of the diode has been introduced, which comprises at least one function of the exponential type.

15 Claims, 8 Drawing Sheets

PROCESS AND DEVICE FOR ANALYZING TRACES OF IMPURITIES IN A GAS SAMPLE BY MEANS OF A DIODE LASER

BACKGROUND OF THE INVENTION (i) Field of the Invention

The present invention relates to the field of the detection of traces of impurities (for example water vapor) in a gas sample. It more particularly relates to the methods for detecting and quantifying such traces of impurities using near-infrared laser spectroscopy.

(ii) Description of Related Art

With regard to the example of detecting water vapor traces, before the appearance of infrared laser spectroscopy analysis techniques (most often referred to in the literature by the term "TDLAS", for "tunable diode laser absorption spectroscopy"), the hygrometers available on the market (whether, for example, dewpoint hygrometers, vibrating-quartz hygrometers or $P_2O_5$ electrolytic hygrometers) offered unsatisfactory performances both relating to the lower detection limit (more than 10 ppb) and relating to the often prohibitive response time of these apparatuses, which may be more than one hour, with an operating time of often more than several hours.

The so-called APIMS method (for atmospheric pressure mass spectrometer) for the first time provided a considerable improvement in the performances achieved in comparison with traditional hygrometers, with a detection limit as low as 10 ppt of water vapor in a neutral gas and a response time of the order of a few minutes for variations in content from one sample to another which can spread over three orders of magnitude.

However, either with traditional hygrometers or APIMS, their operation is relatively incompatible with the measurement of impurities in corrosive gases (such as HCl, HBr, HF, etc.), these hygrometers then having sensitivities of no less than 100 ppb in the optimum case, their performances being largely degraded by the presence of such corrosive gases, and their operation being even sometimes made impossible because of degradation of the instrumentation (incompatibility with the materials).

The appearance of a very wide array of literature has been witnessed over the past few years relating to the TDLAS detection techniques mentioned above, based on the quantification of traces of impurities (for example water vapor) by measuring the optical absorption intensity of the impurity molecules in question in the infrared, the principle of which is as follows: the impurity absorbs light at certain wavelengths, knowledge of these wavelengths and the intensity and the profile of the corresponding absorption lines (having the appearance of a Lorentzian) makes it possible to identify the presence of the molecule and to quantify this presence in the medium analyzed.

Still using the example of the detection of the water molecule, the laser source (most often a semiconductor diode laser) can emit light at a very precise wavelength in the near infrared, which wavelength can be varied by adjusting the temperature and the supply current of the diode.

The Beer-Lambert law is most often used to express the intensity of the light transmitted by the gas medium which comprises the impurity molecules, as attenuated at the characteristic wavelengths of these impurity molecules, according to the formula:

$$I(\lambda)=I_0(\lambda)\cdot\exp(-k\cdot N\cdot L/\pi\cdot\gamma)$$

where

N represents the concentration of the absorbing molecule, $I_0$ represents the initial intensity of the beam emitted by the diode, on entry into the gas sample analyzed, k represents the intensity of the absorption line, L represents the path length in the gas sample analyzed, and γ represents the linewidth.

It can therefore be seen that it is possible to detect an impurity by using the diode laser to scan the profile of one of these characteristic absorption lines. It can also be observed that the intensity of the recorded signal will increase as the impurity concentration in the analyzed sample, the intensity of the selected absorption line and the path length of the beam emitted by the diode through the sample of gas analyzed increase.

The first of the three parameters is clearly definitively set by the range of impurity contents in question (for example of the order of ppb). However, it is always possible to select one of the more intense absorption lines in the spectrum of the molecule considered, and to seek to obtain a maximum path length of the beam through the sample to be analyzed (while attempting to have the least possible detrimental effect on the overall bulk of the apparatus).

This formulation also shows that, for weak absorptions, the concentration of absorbing impurity in the analyzed sample can be deduced linearly from the absorbance measurement for the line considered.

As previously indicated, this principle has been used very widely over the last few years in works relating to the detection of traces of water vapor, the diode laser being set to a wavelength lying around 1.37 μm, or else to the detection of traces of $CH_4$ or $N_2O$ (reference may, in particular, be made to the following works: D. Cassidy, et al., published in Applied Optics, July 1982, p. 2527; J. Mucha et al., published in ISA Transactions, 1986, Vol. 25, p. 25; G. Devyatykh et al., published in SPIE Vol. 1724, Tunable Diode Laser Applications, p. 335; and S. Bone et al., published in Applied Spectroscopy, 1993, Vol. 47, p. 834).

Examination of the performances reported in these various works demonstrates the following points:

- since the use of pressures close to atmospheric pressure or greater than this atmospheric pressure leads to a broadening and an amplitude decrease in the absorption lines, these works have most often selected low-pressure operating conditions;
- such low-pressure conditions then undeniably represent a major drawback for an application of the method to industrial conditions, in which in situ measurements are often desired;
- these low-pressure conditions moreover represent drawbacks associated with the complexity, cost and special requirement of the process, and also through the use of pumps which they require, problems of vibrations which are difficult to control and are not without consequences as regards the detection limit achieved;
- the reported detection levels remain very high (typically several tens of ppm), the very low levels sometimes reported being always projected (extrapolation of results already obtained);
- since these results relate to the detection of water vapor in neutral gases, no information is given regarding the compatibility of such methods with corrosive gaseous media, and in any case the use of vacuum pumps appears incompatible with such corrosive atmospheres;

the achieved detection levels and the lack of compatibility with the presence of corrosive gases therefore make these methods inapplicable to the case of gas lines of microelectronics manufacturers, for which the detection levels to be achieved must be of the order of 1 ppb, in widely varied carrier gases, whether they are inert gases (nitrogen, argon, etc.), or relatively corrosive special gases according to each particular case ($SiH_4$, HBr, HCl, etc.).

SUMMARY AND OBJECTS OF THE INVENTION

In this context, the object of the present invention is to provide a method for analyzing traces of at least one impurity in a gas sample:

making it possible to achieve detection levels as low as 1 ppb;

regardless of the characteristics of the gas sample containing the impurity (whether it is, for example, a neutral gas or reactive special gases for electronics);

which is easy to use in an industrial environment, and therefore, in this regard, has characteristics of small bulk and reduced weight (transportable or even portable apparatus);

very easy and quick to use (for example a reasonable purge time at least less than 30 minutes), and a short response time (of the order of a few seconds); and which is compatible with operation at or above atmospheric pressure (in practice, a few bar).

The work carried out by the Applicant Company in this field has demonstrated that it was possible to provide a solution with a good compromise between these objectives, some of which are, however, conflicting.

This solution, based on the principle of semiconductor diode laser infrared spectroscopy, employs the splitting of the beam emitted by the diode into at least two branched beams, one, called the measurement beam, encountering the gas sample to be analyzed, which is at a pressure at least equal to atmospheric pressure (along a so-called measurement path), and the other, called the reference beam, not encountering this gas sample (along a so-called reference path), the optical path lengths of the measurement and reference paths being equalized respectively between the diode and a measurement photodetector present at the end of the measurement path, and between the diode and a reference photodetector present at the end of the reference path, a modulation of the wavelength emitted by the diode, comprising at least one function of the exponential type, having been introduced.

The work carried out by the Applicant Company, in particular in the field of the detection of traces of water vapor, has in fact demonstrated the importance of the fact of having equalized in air the optical path lengths of the measurement and reference paths in order to access detection limits of the order of 1 ppb, this being in order to overcome the contribution to the measured signal of the humidity in the ambient air. The particular modulation comprising an exponential component moreover advantageously makes it possible to accommodate the broadening and the weakening of the absorption line which are induced as a result of operating at a pressure close to atmospheric pressure and, a fortiori, above. This exponential modulation gives results which are improved compared to the modulations conventionally used, which are of squarewave, sinusoidal, triangular, or else ramp shape, leading in particular to highly symmetrical absorption peak shapes which approach the theoretical profile of a perfect Lorentzian.

The method according to the invention analyzes traces of at least one impurity in a gas sample by means of a tunable diode laser. In the method, a measurement is made of the absorption, by the impurity to be detected, of a light beam emitted by the diode. The supply current of the diode comprises a continuous component and a variable component making it possible to introduce a modulation of the emitted wavelength in order to describe all or part of the profile of at least one of the absorption lines of the impurity. The beam emitted by the diode is split into at least two branched beams, of which one, called the measurement beam, is along a measurement path directed toward the gas sample to be analyzed, which it passes through in a multi-passage cell, before being focused onto a measurement photodetector. Another branched beam, called the reference beam, is along a reference path and directly focused onto a reference photodetector without encountering the gas sample. The optical path lengths of the measurement and reference paths, respectively between the diode and the measurement photodetector and between the diode and the reference photodetector, have been equalized in air, the gas sample to be analyzed is at a pressure at least equal to atmospheric pressure, and the introduced modulation comprises at least one function of the exponential type.

According to the invention, the expression "a function of the exponential type" is intended to mean both an actual exponential (for example in $I_0$ (1-A exp. (-αt))), where A and α represent constants, and t represents time) and a nonlinear sum of polynomials (since, as is known, an exponential function can be mathematically decomposed into a sum of polynomials).

The working pressure according to the invention will advantageously lie in the interval [$10^5$ Pa, $3 \times 10^5$ Pa] absolute but, as will be clearly apparent to the person skilled in the art, a pressure of a few bar more may be encountered in certain cases of industrial pipelines.

The optical path lengths outside the absorption cell are equalized with the aid of an optical path adjustment, the precision of which should be submillimetric or even micrometric. Such an equalization of the optical path lengths may, for example, be obtained by using a system of plane mirrors which are placed on the path of the reference beam and make it possible to vary the optical path length of this reference path between the diode laser and the reference photodetector, without altering the alignment thereof.

As indicated above, the introduced modulation, which comprises a function of the exponential type (for example in $I_0$ (1-A exp. (-αt))) has shown, as will be expounded upon hereafter in the context of examples, results which are substantially improved compared to the modulations traditionally used and recommended in the literature, while permitting better accommodation of the phenomena of broadening and amplitude decrease of the absorption lines, which are induced by operating at a pressure close to atmospheric pressure.

The laser source used will advantageously be a semiconductor diode of the InGaAsP type (the so-called DFB, DBR, DFB/DBR types which are well known to the person skilled in the art) or else a diode of the doped-crystal solid laser type.

As will be clearly apparent to the person skilled in the art, depending on the impurity to be detected in the gas sample to be analyzed, the emission of the diode will be centered on a wavelength corresponding to an absorption line which is advantageous for the impurity in question (for example on the wavelength close to 1.37 μm, or else on a wavelength close to 1.9 μm, for detecting traces of water vapor).

The diode is then advantageously temperature-stabilized (for example by using a Peltier-effect element), in order to center its emission on the selected absorption line, the current used for supplying the diode then making it possible to modulate the wavelength in order to describe all or part of the profile of the absorption line selected for the molecule in question (the supply current of the diode then comprises a continuous component and a variable component, the latter being used to modulate the emitted wavelength).

According to one of the embodiments of the invention, no cell is arranged on the reference path, between the diode and the reference photodetector.

Advantageously, the diode and/or the measurement and reference photodetectors are mounted without a window.

The multipassage cell used is, for example, of the Herriot type, as composed of two spherical mirrors with the same focal length, one of these mirrors comprising an off-centered orifice through which the beam enters and leaves the cell after a certain number of reflections. The input window of the cell is advantageously inclined at the Brewster angle, so that the naturally polarized beam of the diode laser is fully transmitted, while minimizing parasitic reflections which are a source of perturbation of the signal.

A multipassage cell of the astigmatic type, for example, may also be envisaged.

It will be chosen to make the multipassage cell used physically compatible with widely variable gas samples to be analyzed, whether they are gases of very high purity (for example the detection of residual water vapor contents at the level of 1 ppb in nitrogen or argon with very high purity), or else corrosive gases employed in the microelectronics industry, such as HF, HCl, HBr, etc. It will then be chosen to make the cell, and also the mirrors of which it is composed, from materials which firstly have high compatibility with corrosive gases, such as nickel or else HAS-TELLOY (a series of high-strength, nickel-base, corrosion resistant alloys), and also a very low degassing/desorption factor for the molecules to be detected.

It will also be chosen to construct the cell according to the rules relating to ultravacuum conditions or gases of very high purity, favoring metallic materials and avoiding polymer materials, including for the seals, except when their use proves necessary (in particular around the window).

According to a preferred embodiment of the invention, the cell is made from a single metal block (thus machined from solid), without welded joints or weld beads, which represent points which are potentially vulnerable to corrosion.

Still with the aim of minimizing optical noise and other parasitic reflections, it may, for example, be chosen to use, for the component used to split the beam emitted by the diode into as many branched beams as desired, a splitter component (for example a splitter plate) which is thin and perfectly cleared. It is also possible to incline the detectors sufficiently to limit reflections toward the diode laser and to clear the rear face of this diode laser, and also, in general, to prevent the beams from being diaphragmed downstream of the splitter component at any moment.

In order to achieve the aim of a detection limit which is as low as 1 ppb (for example 1 ppb of water vapor), it is advantageous, as a complement to the equalization of the analysis/reference optical path lengths already mentioned above, to flush the space contained between the diode laser and each detector with a protective gas, this protective gas flow making it possible, on the one hand, to reduce the parasitic signal due to the presence of impurities in the detection head, and also to increase the transmitted optical power, because of the reduced absorption by the presence of such parasitic impurities.

Such flushing with a protective gas (advantageously nitrogen or else argon) will advantageously be implemented by including the assembly constituted by the diode, the measurement and reference photodetectors and the multipassage cell containg the gas to be analyzed in a hood, which is isolated from the surrounding atmosphere, and which will be flushed with such a protective gas flow. The absence of a window at the detectors and the diode then represents a very positive point as regards the limitation of the presence of any unpurged dead volumes.

Such flushing with the protective gas will advantageously be carried out in laminar flow, in order to improve the efficiency and stability of the flow, and also to optimize the gas consumption.

In order to favor the obtaining of improved response times for the method, it appears quite particularly advantageous to minimize the residence time of the molecules of the gas sample to be analyzed in the cell, which the Applicant Company has obtained according to the invention by minimizing the dead volumes and the vortex phenomena when the gas enters the cell and when it flows through this cell, ensuring a laminar or quasi-laminar flow of the gas in the cell. An illustration of embodiments making it possible to obtain such a laminar flow is given further on in the present description.

The invention also relates to an apparatus for analyzing traces of at least one impurity in a gas sample, suitable for implementing the invention, comprising, a semiconductor diode laser;

at least one splitter system making it possible to split the beam emitted by the diode into at least two branched beams, one called the measurement beam and the other called the reference beam;

a multipassage cell containing the gas sample to be analyzed;

an optical device making it possible to direct the measurement beam along a measurement optical path onto the multipassage cell;

a measurement photodetector;

an optical device making it possible to direct the measurement beam output by the multipassage cell onto the measurement photodetector;

a reference photodetector;

an optical device making it possible to direct the reference branched beam along a reference optical path onto the reference photodetector;

elements for acquisition and processing of the beams generated by the two photodetectors, the apparatus comprising means making it possible to equalize the optical path lengths of the measurement and reference paths, respectively between the diode and the measurement photodetector, and between the diode and the reference photodetector, and which device comprises means for modulating the supply current of the diode, making it possible to introduce a modulation comprising at least one function of the exponential type.

The equalization means may, for example, comprise systems of plane mirrors present on the reference path between the splitter system and the reference photodetector.

According to one of the aspects of the invention, the apparatus comprises a Peltier-effect element making it possible to stabilize the temperature of the diode.

The diode and/or the measurement and reference photo-detectors are advantageously without a window.

The assembly consisting of the diode, the measurement and reference photodetectors and the multipassage cell which comprises the gas to be analyzed will advantageously be isolated from the surrounding atmosphere, by including it in a hood, this hood being provided with means making it possible to flush the interior of the hood with a protective gas flow. The means used for carrying out this flushing will advantageously be dimensioned in such a way that the flushing produced is substantially laminar.

Porous channels may, for example, be envisaged for obtaining such a substantially laminar regime. Reference may also be made to the work carried out by the Applicant Company, relating to the gas injection systems for the production of protective atmospheres in confined spaces (French Patent Application No. 93.15503 of 22 Dec. 1993).

The cell will advantageously be in the form of a single metal block machined from solid (and therefore without a welded joint or weld bead).

According to one of the aspects of the invention, the points where the gas is injected into the cell and where the gas leaves the cell are designed in such a way as to establish a substantially laminar flow regime of the gas to be analyzed in the cell.

Other features and advantages of the present invention will emerge from the following description of embodiments which are given by way of illustration but without implying any limitation, made with reference to the appended drawings, in which:

DETAILED DESCRIPTION OF PREFERRED EMBODIMENTS

Figure 1:
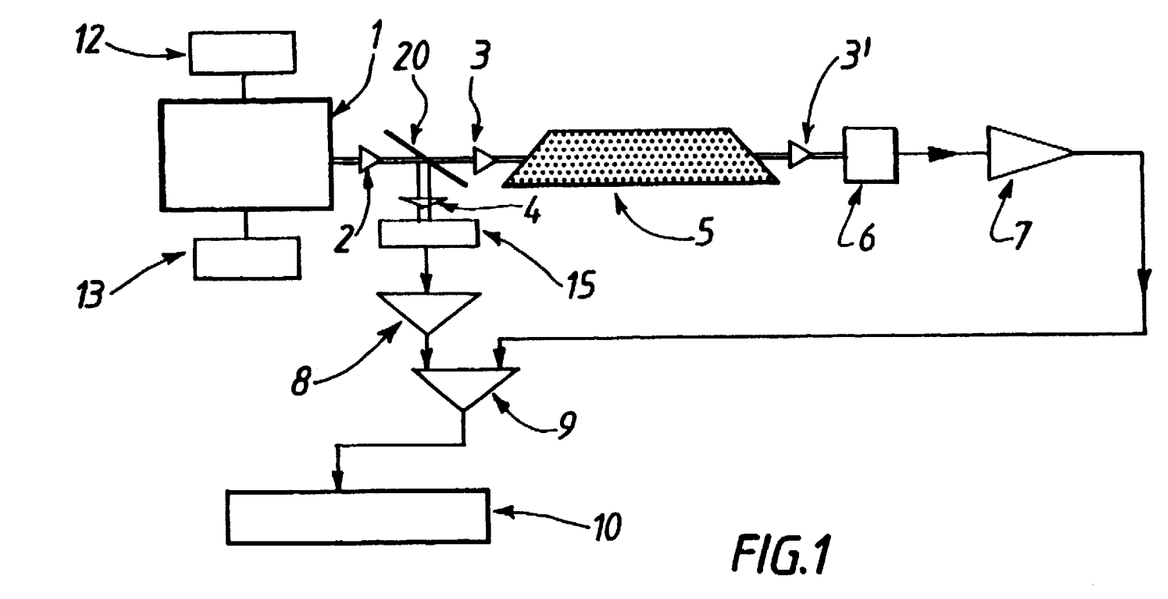
FIG. 1 is a schematic representation of an installation suitable for implementing the invention.

FIG. 1 schematically illustrates the path of measurement and reference beams from the diode to the data acquisition and processing system. A tunable semiconductor diode 1 (here of the InGaAsP type) emits a beam 2 which is split by a splitter plate 20 into an undeviated measurement beam 3 and a reflected reference beam 4.

The diode is temperature-stabilized, for example at a temperature close to ambient temperature, by using a Peltier-effect element 12.

It is supplied by a current generator 13 with a current comprising a continuous component and a variable component used to modulate the wavelength of the beam emitted by the diode, in order to describe all or part of the profile of the absorption line selected for the molecule analyzed.

The measurement beam 3 is aligned so as to be injected into a cell 5, advantageously of the Herriot type (containing the gas sample to be analyzed) at a given point and with given directional coefficients. The window for input into the cell 5 is advantageously inclined at the Brewster angle, in order for the naturally polarized beam to be fully transmitted.

The measurement beam 3' obtained at the output of the cell is focused onto a detector 6 (for example InGaAs or else Ge).

The current generated by the photodetector 6 is preamplified on a transimpedence amplifier 7, the voltage signal resulting therefrom being sent to a differential amplifier 9.

Figure 2:
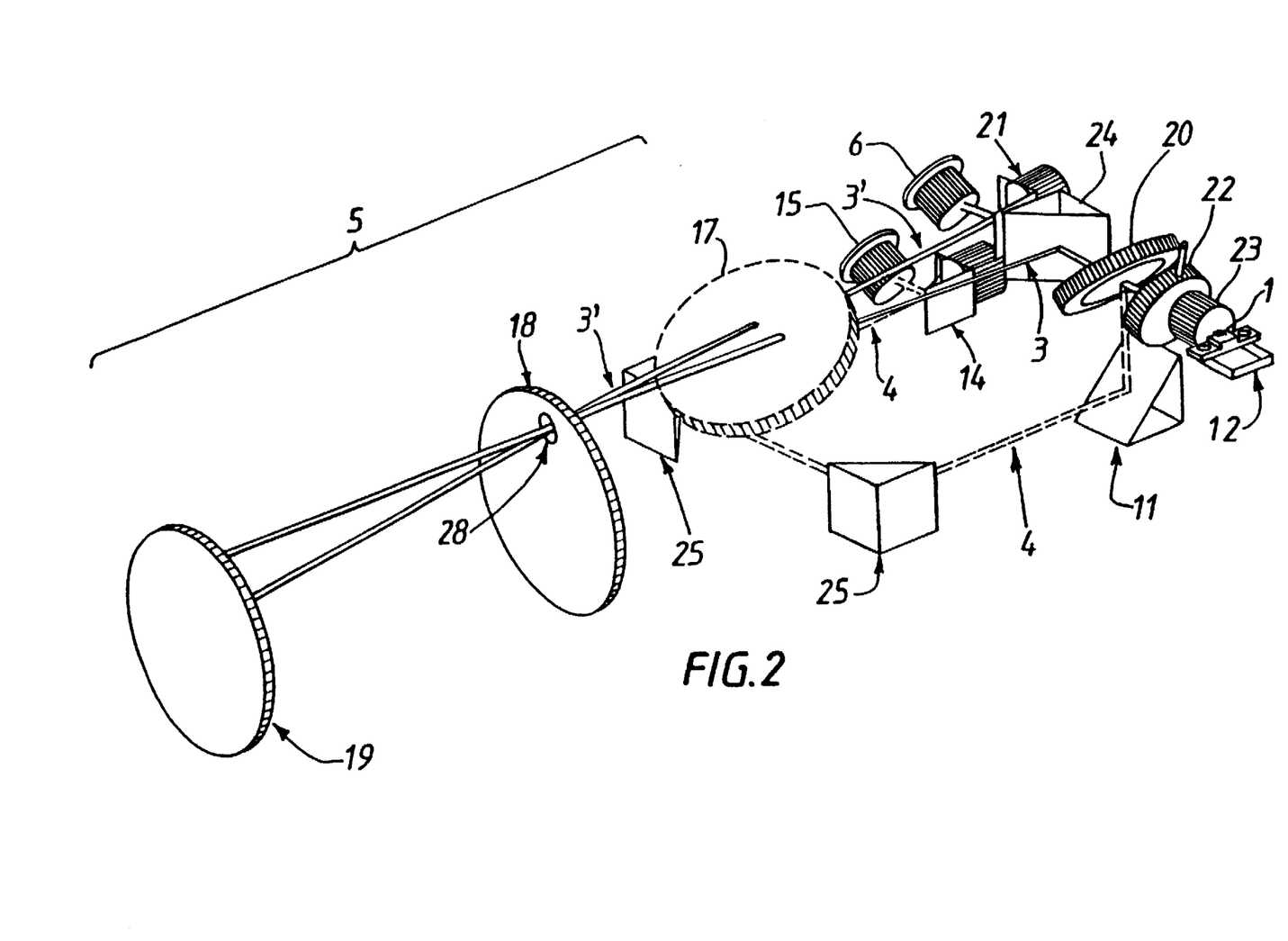
FIG. 2 is a schematic representation of some of the optical elements found on the path of the measurement and reference beams.

For its part, the reference beam 4 is directed onto a system of mirrors (not represented in this figure) which focus the beam onto a photodetector 15, and which also makes it possible to vary the optical path length of the reference path between the diode laser and the detector 15, without altering its alignment, thus making it possible to equalize the optical path lengths of the reference and measurement paths in air (the optical elements involved in this equalization of the optical path lengths of the measurement and reference paths will be detailed further on in the context of FIG. 2).

The current generated by the photodetector 15 is here again preamplified on a transimpedence amplifier 8, the voltage signal resulting therefrom being sent to the differential amplifier 9, mentioned above, which performs subtraction with the signal output by the preamplifier 7, in order to reconstruct the profile of the absorption line of the impurity traces in the gas sample analyzed.

For the embodiment represented, the beams are subtracted after each beam has been preamplified, on a transimpedence amplifier (7, 8). One variant could consist in performing the subtraction, followed by the preamplification of the signal obtained during the subtraction operation.

The signal resulting therefrom is sent towards a data acquisition and integration system 10, where this signal is filtered, sampled and converted into a digital signal, then stored in memory, this being done for each of the wavelengths scanned in the absorption line by the signal emitted by the diode 1. The operation is thus repeated for each of the these wavelengths and the corresponding signals are added to the previous ones, with the aim of improving the signal/noise ratio. This operation is advantageously repeated for as many times as is necessary in order to obtain a favorable signal/noise ratio.

FIG. 2 provides the detail of the optical elements encountered by the measurement 3 and reference 4 beams between the diode 1 and the data acquisition and processing system 10.

The diode laser 1 emits a beam which is directed toward the splitter plate 20, in this case passing through collimation optics 23 and a diaphragm 22, the emitted beam being split into the measurement 3 and reference 4 beams.

The measurement beam 3 encounters a mirror 24 before reaching the multipassage cell 5, through its input window 17 which, in the example represented, is inclined at the Brewster angle. This cell 5 is of the Herriot type and, for the embodiment represented, is composed of two spherical mirrors 18 and 19 with the same focal length, one of these mirrors comprising an off-centered orifice 28 through which the beam 3 enters and leaves the cell (the output beam is denoted 3') after N reflections. The beam 3' emerging from the multipassage cell 5 is directed via a parabolic mirror 21 onto the measurement photodetector 6.

For its part, the reference beam 4 output by the splitter 20 is directed, via a system of plane (11, 25) and parabolic (14) mirrors, onto the reference photodetector 15. The system of plane mirrors 25, which is mounted on a translation plate, makes it possible to vary the optical path length of the reference path between the diode laser and the reference photodetector 15, without altering its alignment, in order to obtain equalization of the optical path lengths of the reference and measurement paths.

Figure 3:
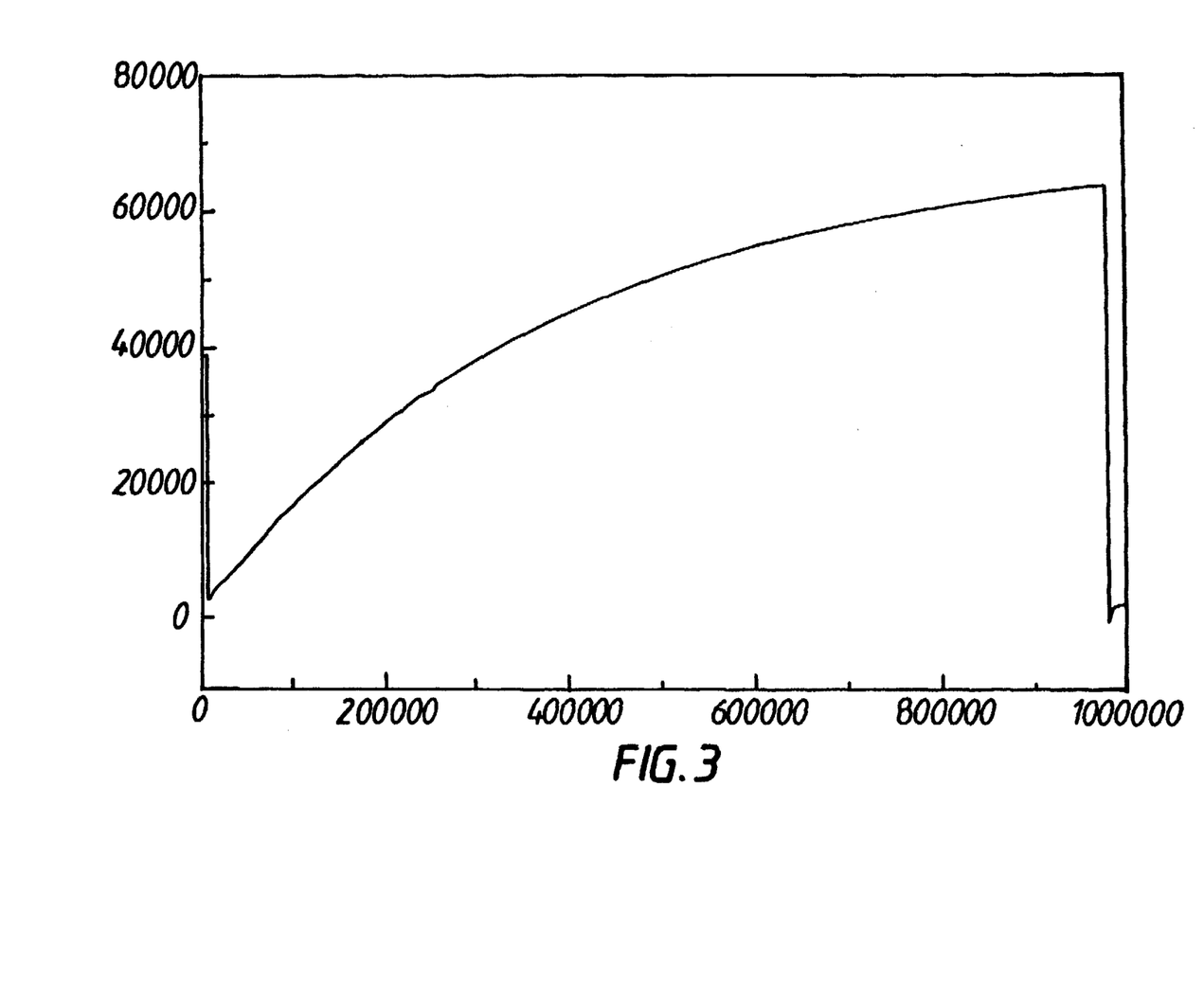
FIG. 3 is a representation of an example of a modulation function of the current of the diode laser, comprising an exponential component.

FIG. 3 illustrates an example of a modulation function of the current supplying the diode laser 1, set up using the current generator 13. The represented example illustrates the case of a modulation function of the type 1-A exp. (−2.5 t) with a period of 1 kHz.

In this case, the modulation is represented with arbitrary units both on the abscissa and on the ordinate (for a time unit for the abscissa and a voltage unit for the ordinate).

Figure 4:
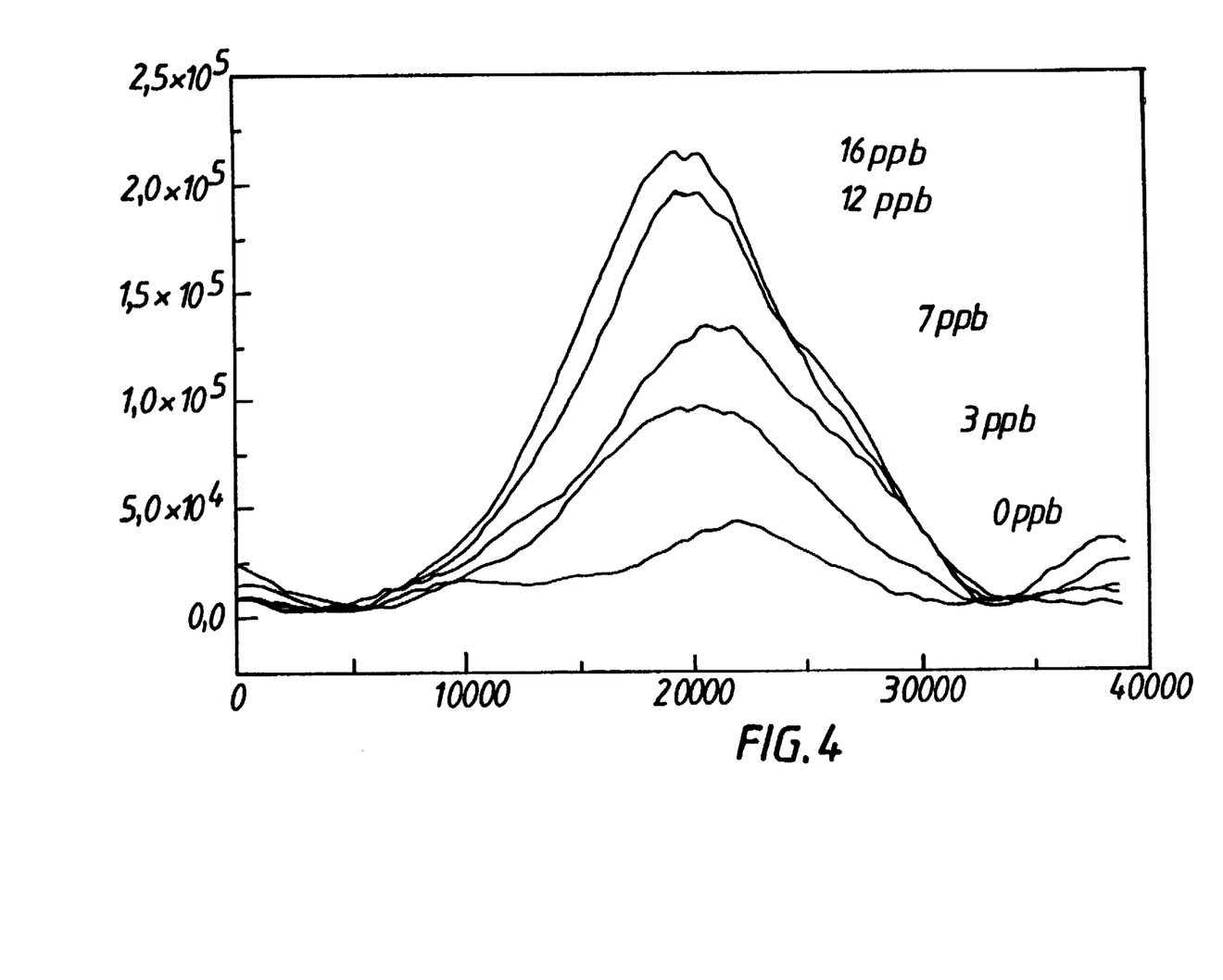
FIG. 4 illustrates the results obtained, in the case of using an exponential modulation in 1-exp (−2.5 t) for various $H_2O$ concentrations present in the gas sample to be analyzed.

FIG. 4 illustrates the results obtained for various exemplary embodiments of an installation as described in the context of FIGS. 1 and 2, and in the case of detecting traces of water vapor in a nitrogen sample to be analyzed. The modulation function used here had the form 1-exp. (−2.5 t), the temperature of the diode being regulated so as to adjust the wavelength of the diode laser emission around that absorption line of water vapor which is close to 1.37 μm (coverage of the spectral band, approximately 1.364 μm to 1.372 μm).

For each example of water vapor content detected, the represented signal corresponds to the difference between the measurement and reference beams obtained. The operation of scanning the aforementioned wavelength range was repeated 96,000 times for each of the cases treated (acquisition of the signal, processing, storage in memory and addition to the previous signals).

The five signals correspond to water vapor contents in nitrogen ranging from 0 ppb (simple flushing of the cell with ultrapure nitrogen, this "0" ppb thus having to be considered as qualifying the subtraction of two beams which have encountered the same nitrogen atmosphere) to 16 ppb, while passing through intermediate contents corresponding to 3, 7 and 12 ppb of water vapor in nitrogen. These water vapor contents were introduced into the reference nitrogen by using permeation cartridges.

For all these exemplary embodiments, the entire detection head (diode, multipassage cell, detectors) was placed in a hermetic hood flushed by a dry nitrogen gas flow.

Here again, the representation in FIG. 4 uses arbitrary units both on the abscissa and on the ordinate (corresponding to time units on the abscissa and voltage units on the ordinate).

FIG. 4 shows the presence, for the curve "0 ppb" of weak absorption (presence of a small rise in the curve), which may correspond to a possible water vapor residue in the cell, or else (possibly in combination with the previous reason) to a slight imperfection in the equalization of the optical path lengths, or else to a water vapor content which is not perfectly homogeneous over time and/or through space in the detection head or in the cell.

It is then satisfying to observe that, despite this slight imperfection (which it is possible to remedy or else which can be taken into account), an emphatic differentiation in the signals obtained in each concentration case is observed, even at the lowest levels, since it is perfectly possible to differentiate between the curves obtained for 0,3 and 7 ppb.

Figure 5:
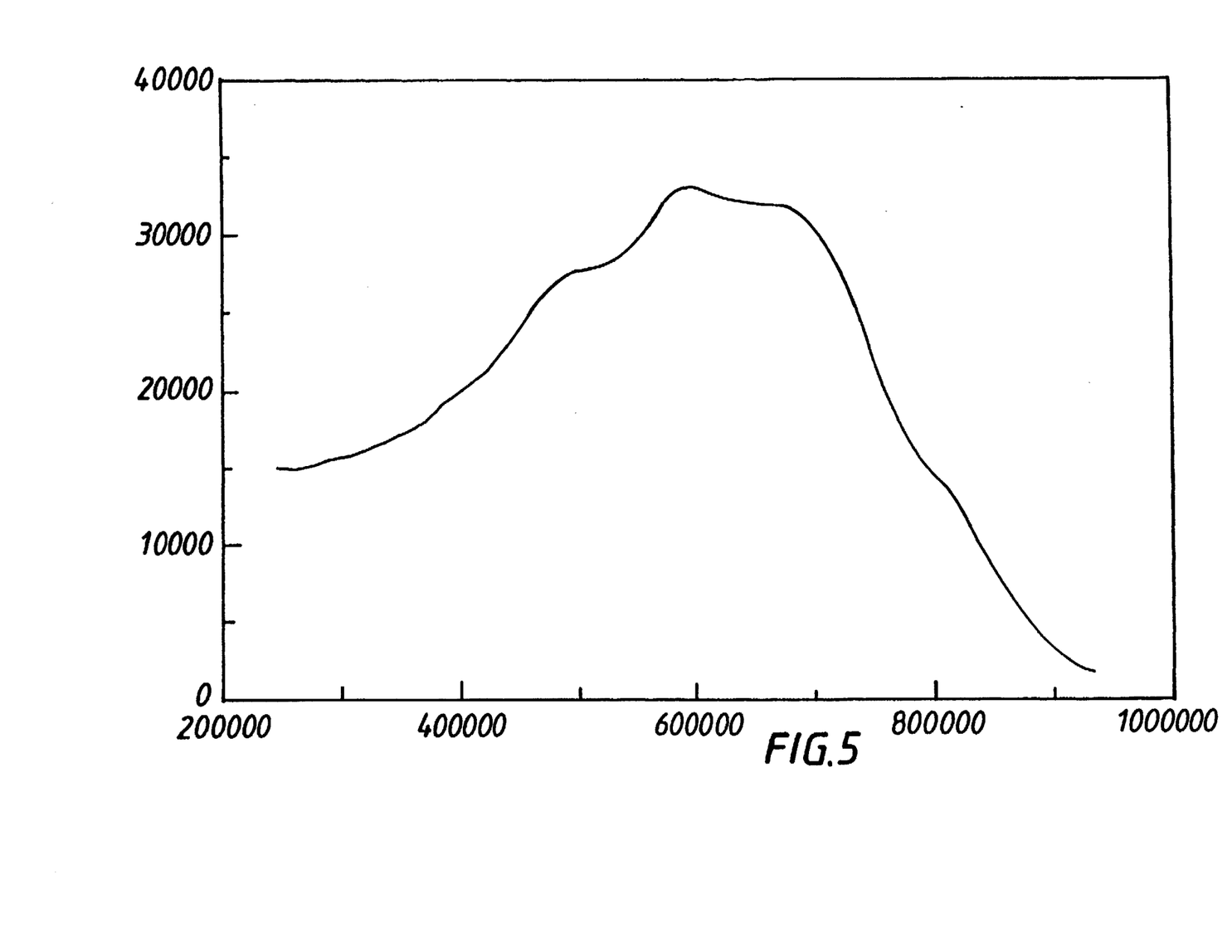
FIGS. 5 and 6 illustrate the comparative results of the signal obtained in the absence of water vapor in the gas sample to be analyzed (flushing the cell with nitrogen), respectively using a sawtooth modulation (A t+B) and an exponential modulation (1-exp. (−2.5 t))
Figure 6:
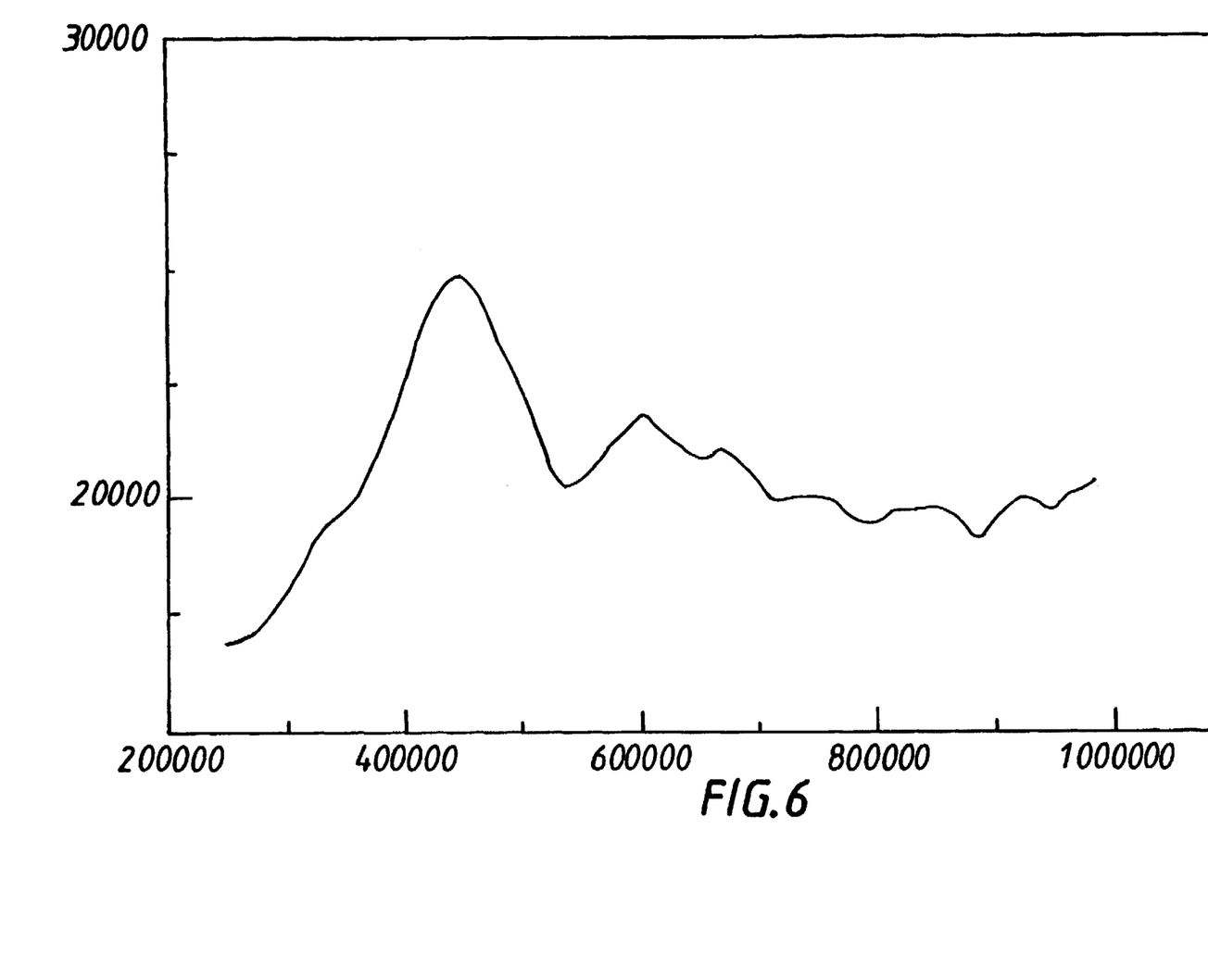

FIGS. 5 and 6 illustrate, in the case when water vapor is not introduced into the gas to be analyzed (simple flushing with dry nitrogen), the comparative results observed for the use of an exponential modulation function (modulation in 1-exp. (−2.5 t)) as replacement for a traditional sawtooth modulation.

FIG. 5 (case of a sawtooth modulation) then illustrates the particularly significant thickening obtained in the case when such a sawtooth modulation is used, even in the "absence" of water vapor in the nitrogen gas sample analyzed.

Figure 7:
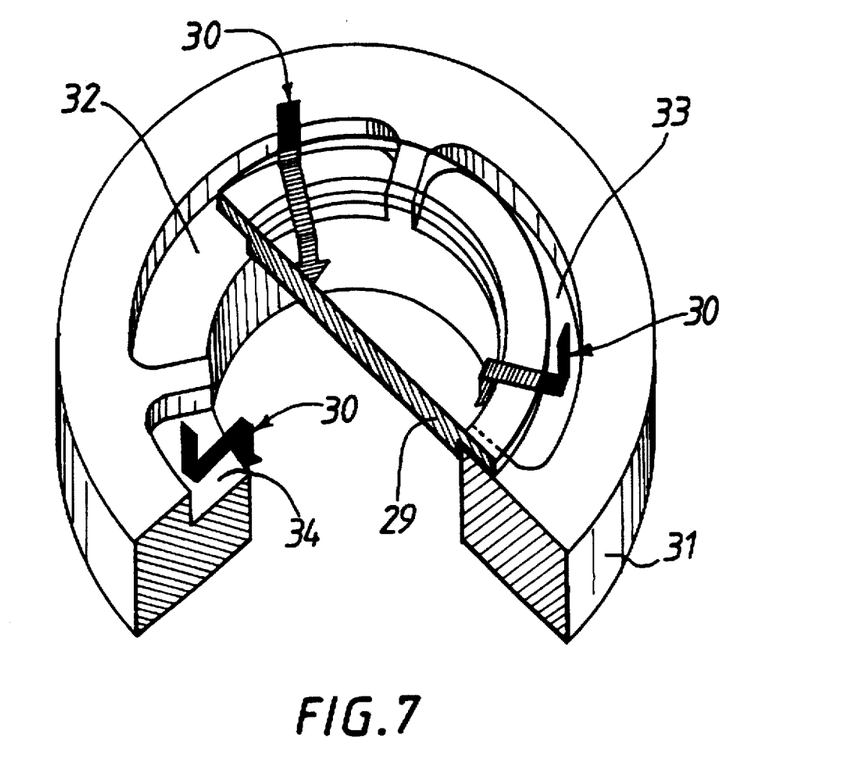
FIGS. 7 and 8 illustrate an exemplary embodiment of a laminar flow regime of the gas to be analyzed in the cell.

FIG. 7 illustrates one of the embodiments for injecting a gas to be analyzed into a cell 31 with cylindrical geometry, which has made it possible to successfully obtain a laminar flow regime of the gas in the cell. FIG. 7, which is a partial section of the input of the cell 31, demonstrates an input mirror 29 (it will be noted that only half of the mirror has been represented in order to simplify the representation and thus to aid visualization). The cell 31 has, at its input face and below the mirror, three gas-injection cutouts 32, 33, 34 in the shape of portions of a ring (type of corolla) which are angularly distributed approximately symmetrically about the axis of the cell. The gas to be analyzed, which arrives at the input of the cell, then passes under the mirror, inside each cutout, before entering the cylindrical body of the cell. In order not to overburden the figure, the flow of the gases has been illustrated by simple arrows 30, there being three arrows, one per cutout.

Figure 8:
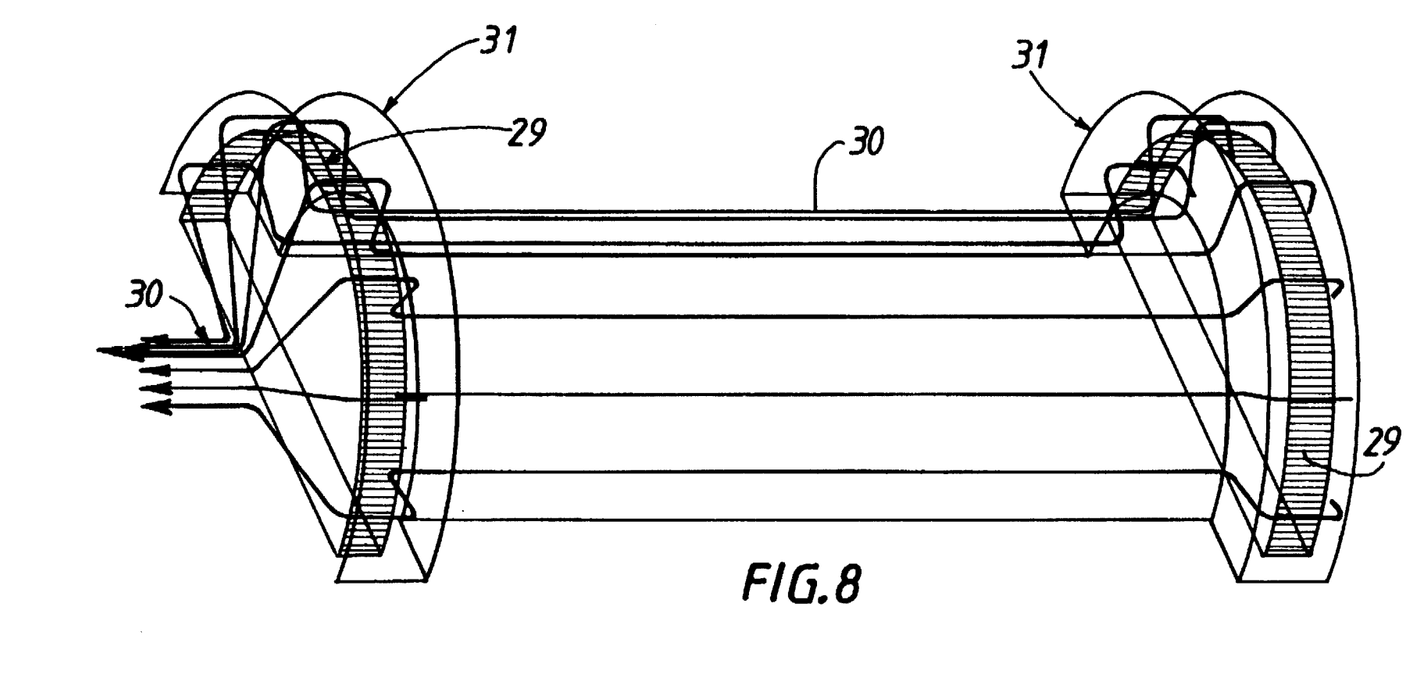

FIG. 8 illustrates a schematic representation of a simulation of the gas flow obtained in such a configuration, between the input and the output of the cell, with the gas circumventing the mirror in each case. For the sake of simplification, the injection cutouts have not been represented in this figure, it being instead chosen to symbolize the result obtained, which is the absence or the marked reduction of the vortex phenomena, and the flow of the gas inside the cell in a substantially laminar regime.

FIGS. 7 and 8 illustrate only one of many possible alternative embodiments of the gas inlet and outlet means of the cell which make it possible to obtain such a substantially leminar flow. Further configurations, such as, for example, the use of circular injection orifices distributed approximately regularly about the axis of the cell, could be envisaged.

Although the present invention has been described with reference to particular embodiments, it is in no way limited thereby and, on the contrary, is capable of modifications and variants which will occur to a person skilled in the art.

Thus, although the case of detecting traces of water vapor has quite particularly been mentioned and exemplified above, it will be understood that the present invention applies much more broadly to other impurities that can be detected by absorption. Mention in this regard be made of the detection of HF and $WF_6$ by using, for example, the quite particularly advantageous HF line situated at approximately 1.3618 μm. Since HF is produced in a $WF_6$ tank by a reaction between $WF_6$ and $H_2O$, the quantification of HF therefore makes it possible to indirectly quantify the decomposition of $WF_6$, and therefore the initial quantity of water vapor present in the tank.

Similarly, as regards the carrier gas, the examples discussed above quite particularly illustrated the case of a nitrogen carrier gas (detection of traces of water vapor on the scale of 1 ppb or several ppb in nitrogen). It should, however, be noted that the work completed by the Applicant Company has demonstrated that the process and device according to the invention also make it possible to achieve such detection limits on the scale of a few ppb in the case of detecting traces of water vapor in chemical gases such as $CF_4$, $SF_6$ or else $NF_3$.

We claim:

1. A process for analyzing traces of at least one impurity in a gas sample by means of a tunable diode laser comprising the steps of:

measuring absorption, by the impurity to be detected, of a light beam emitted by a diode laser, wherein said diode laser is supplied with a supply current comprising a continuous component and a variable component effective to introduce a modulation of the emitted wavelength in order to describe all or part of a profile of at least one absorption line of said impurity, splitting the beam emitted by the diode laser into at least two branched beams comprising (i) a measurement beam along a measurement path directed toward the gas sample to be analyzed, which passes through said gas sample in a multipassage cell before being focused onto a measurement photodetector and (ii) a reference beam along a reference path and directly focused onto a reference photodetector without encountering the gas sample, wherein (a) the measurement and reference paths, respectively have optical path lengths between the diode laser and the measurement photodetector and between the diode laser and the reference photodetector, which have been equalized in air, (b) said gas sample is at a pressure at least equal to atmospheric pressure, and (c) said introduced modulation comprises at least one function of the exponential type.

2. The process as claimed in claim 1, wherein said gas sample has a pressure which does not exceed $3 \times 10^5$ Pa absolute.

3. The process as claimed in claim 2, wherein said pressure of said gas sample ranges between $10^5$ Pa and $3 \times 10^5$ Pa absolute.

4. The process as claimed in claim 1, further comprising the step of flushing a space contained between the diode laser and each photodetector with a protective gas.

5. The process as claimed in claim 4, wherein said flushing is carried out in laminar flow.

6. The process as claimed in claim 1, wherein said impurity analyzed is water.

7. The process as claimed in claim 6, wherein the modulation introduced in the emitted wavelength extends around one of the following two wavelengths: 1.37 μm or 1.9 μm.

8. Device for analyzing traces of at least one impurity in a gas sample comprising, a semiconductor diode laser which emits a beam;

at least one splitter system effective to split the beam emitted by the diode laser into at least two branched beams comprising, a measurement beam and a reference beam;

a multipassage cell containing the gas sample to be analyzed;

an optical device effective to send the branched measurement beam output by the splitter system along a measurement optical path onto the multipassage cell;

a measurement photodetector which generates a signal;

an optical device effective to direct the measurement beam output by the multipassage cell onto the measurement photodetector;

a reference photodetector which generates a signal;

a device effective to direct the reference branched beam output by the splitter system along a reference optical path onto the reference photodetector;

element for acquisition and processing of the signals generated by the measurement and reference photodetectors;

means for equalizing optical path lengths of the measurement and reference paths, respectively between the diode laser and the measurement photodetector, and between the diode laser and the reference photodetector, and supply current of the diode laser and means for modulating the supply current of the diode laser, effective to introduce a modulation comprising at least one function of the exponential type.

9. The device as claimed in claim 8, wherein said means for equalizing the optical path lengths comprises systems of mirrors present on the reference path between the splitter system and the reference photodetector.

10. The device as claimed in claim 8, further comprising means for stabilizing the temperature of the diode laser.

11. The device as claimed in claim 8, wherein at least one of the diode laser and the measurement and reference photodetectors is without a window.

12. The device as claimed in claim 8, wherein an assembly comprising the diode laser, the measurement and reference photodetectors and the multipassage cell comprising the gas to be analyzed is isolated from a surrounding atmosphere by being located in an inert gas flow.

13. The device as claimed in claim 12, wherein the means for injecting a gas flow is dimensioned in such a way that said gas flow is substantially laminar.

14. The device as claimed in claim 8, wherein the cell is made from a single-piece metal block.

15. The device as claimed in claim 8, wherein the cell further comprises a means for inlet of the gas to be analyzed into the cell, and for outlet of the gas to be analyzed from the cell, effective to establish a substantially laminar flow regime of the gas inside the cell.

* * * * *